US012796970B2

(12) United States Patent
Nørgaard et al.

(10) Patent No.: US 12,796,970 B2
(45) Date of Patent: Nov. 17, 2026

(54) AIR-PUMP ARRANGEMENT FOR AN ACOUSTIC MEASUREMENT DEVICE

(71) Applicant: Interacoustics A/S, Middelfart (DK)

(72) Inventors: Kren Monrad Nørgaard, Middelfart (DK); Jonas Sjursen, Middelfart (DK)

(73) Assignee: Interacoustics A/S, Middelfart (DK)

( * ) Notice: Subject to any disclaimer, the term of this patent is extended or adjusted under 35 U.S.C. 154(b) by 486 days.

(21) Appl. No.: 18/339,254

(22) Filed: Jun. 22, 2023

(65) Prior Publication Data

US 2023/0414133 A1 Dec. 28, 2023

(30) Foreign Application Priority Data

Jun. 23, 2022 (EP) .................................... 22180714

(51) Int. Cl.
*A61B 5/12* (2006.01)
*A61B 1/227* (2006.01)
*A61B 5/00* (2006.01)

(52) U.S. Cl.
CPC ............ *A61B 5/126* (2013.01); *A61B 1/2275* (2013.01); *A61B 5/125* (2013.01); *A61B 5/6817* (2013.01)

(58) Field of Classification Search
CPC ..... A61B 5/125; A61B 5/6817; A61B 5/6815; A61B 5/121; A61B 5/12; A61B 1/2275; A61B 1/227; A61B 2562/0204; G01H 15/00; G01H 17/00
See application file for complete search history.

(56) References Cited

U.S. PATENT DOCUMENTS

2003/0171655 A1* 9/2003 Newman ................ A61B 1/227 600/200
2006/0019741 A1 1/2006 Tobin
2015/0003644 A1* 1/2015 George ............... A61M 13/003 381/165
2015/0034250 A1 2/2015 Masuda et al.
2015/0342504 A1* 12/2015 Lantz ..................... A61B 5/121 73/585
2016/0220155 A1* 8/2016 Bojesen ................. A61B 5/126
2019/0274917 A1* 9/2019 Avni ...................... A61H 9/005

FOREIGN PATENT DOCUMENTS

DE 102005017091 10/2006
WO 2021/149036 7/2021

OTHER PUBLICATIONS

IEC 60645-5, 2005 "Instruments for the measurement of aural acoustic impedance/admittance. (International Electrotechnical Commission, Geneva, Switzerland)".

* cited by examiner

*Primary Examiner* — Karen E Toth

(57) ABSTRACT

Disclosed herein are embodiments of an acoustic measurement device configured to provide acoustic property values for objective ear-condition evaluation of a patient's ear, in particular a human's ear. Said acoustic measurement device can be configured to be positioned within an ear canal of said patient and configured to take a resting position within said ear canal. Embodiments of the acoustic measurement device can include an air-pump arrangement, said air-pump arrangement, at least in said resting position, being in fluid connection with said ear canal through at least one tube running via said ear probe.

12 Claims, 4 Drawing Sheets

AIR-PUMP ARRANGEMENT FOR AN ACOUSTIC MEASUREMENT DEVICE

FIELD

The present application relates to an acoustic measurement device configured to provide acoustic property values for objective ear-condition evaluation of a patient's ear, wherein at least part of the acoustic measurement device being configured to be positioned within an ear canal of the patient and configured to take a resting position within the ear canal. The acoustic measurement device comprises an ear probe and the acoustic measurement device comprises an air-pump arrangement. The air-pump arrangement, at least in the resting position, being in fluid connection with the ear canal through at least one tube running via the ear probe. The air-pump arrangement, in the resting position, is configured to apply an air-pressure control procedure, consisting of at least one air-pressure level, across the patient's tympanic membrane of the ear, wherein the acoustic measurement device, in the resting position, being configured to provide acoustic property values in reaction to the air-pressure control procedure applied by the pump arrangement across the patient's tympanic membrane of the ear.

The application further relates to a diagnostic instrumental arrangement configured to provide at least one objective ear-condition parameter of a patient's ear comprising an acoustic measurement device according to the application, further comprising an acoustic input unit configured to capture acoustic signals representative for the air-pressure levels within the ear canal, a control device configured to control the pump arrangement, and a processing device configured to further process the captured acoustic signals to an evaluation device, the evaluation device being configured to execute an evaluation process to the processed acoustic signals associated to the air-pressure control procedure to obtain the at least one objective ear-condition parameter for the patient's ear.

Moreover, the present application relates to an objective ear-condition evaluation method using a diagnostic instrumental arrangement according to the application.

BACKGROUND

Acoustic measurement devices and diagnostic instrumental arrangements are known in the art for example from tympanometric diagnostic methods, diagnostic methods for pressurized acoustic-reflex measurement, or diagnostic methods for otoacoustic-emission measurement. Those instruments known in the art for hearing diagnostics conventionally utilize piston, peristaltic, or gear pumps. These pumps are characterized by being driven by an electric motor, and operating the motor at some constant power generates a constant volume-displacement rate.

These pumps offer suitable performance when it comes to perform air-pressure control procedures as they are for example standardized for several diagnostic type instruments in IEC 60645-5 (2005), thereby operating—even in the case of tympanometry—within a rather small pressure-difference region (with magnitudes up to 600 daPa) relative to the absolute ambient pressure (approximately 10132.5 daPa), resulting in an approximately constant-rate pressure sweep usually requiring no or little regulation.

However, these pumps have several less-desirable properties such as their mechanical complexity, their large size, and their relatively slow responsiveness due to the internal mass which needs to move before the pressure changes. In particular, as regards the application of a piston pump, the respective acoustic measurement device then further suffers from its inherent displacement limits.

Therefore, there is a need to provide a solution that addresses at least some of the above-mentioned challenges that come along with the known acoustic measurement devices and their air-pump arrangement.

SUMMARY

Thus, it is the object of the present application to provide an acoustic measurement device and a diagnostic instrumental arrangement as described above, which do not show the disadvantages described above, or at least show them to a lesser extent, and which, in particular, provide a space saving design for an acoustic measurement device, which reduces the overall effort, e.g. in terms of handling the acoustic measurement device and instrumental arrangement during diagnostics, and facilitates simple production of such device, however at the same time providing reliable results for the objective ear-condition evaluation of the patient's ear.

The present application is based on the technical teaching that a more space saving design results, for example, in a more handy operation of the respective instrument. Further, reliable results for objective ear-condition evaluation can be accomplished, if instead of the known pump configurations applied in the field of objective acoustic measurements so far (e.g. piston, peristaltic, or gear pumps), a membrane pump (also known as a diaphragm pump) configuration is used. The membrane pump configuration may (preferably) be formed as a piezo-electric membrane pump configuration (e.g. a miniature piezo-electric membrane pump configuration).

This alternative type of pump, namely a membrane pump and in particular in the form of a miniature piezo-electric membrane pump, generally operates by displacing an elastic element, in particular a membrane, in a harmonic motion.

Usually, in its regular field of application, this pump then relies on internal check valves (i.e., allowing flow in one but not the other direction) to turn this oscillating displacement into an air flow, which enters through an inlet during the first half cycle and exits through the outlet in the second half cycle. Thus, these kind of membrane pumps are known to be inherently unidirectional, a directionality which is defined by the orientation of the check valves.

Hence, according to one aspect, the present application relates to an acoustic measurement device configured to provide acoustic property values for objective ear-condition evaluation of a patient's ear, in particular a human's ear, wherein at least part of said acoustic measurement device being configured to be positioned within an ear canal of said patient and configured to take a resting position within said ear canal, said acoustic measurement device comprising an ear probe, said acoustic measurement device comprising an air-pump arrangement, said air-pump arrangement, at least in said resting position, being in fluid connection with said ear canal through at least one tube running via said ear probe, said air-pump arrangement, in said resting position, being configured to apply an air-pressure control procedure, consisting of at least one air-pressure level, across said patient's tympanic membrane of said ear, wherein said acoustic measurement device, in said resting position, being configured to provide acoustic property values in reaction to said air pressure control procedure applied by said pump arrangement across said patient's tympanic membrane of said ear.

Said air-pump arrangement comprising at least two pumps, wherein said at least two pumps comprising a movable element in the form of a membrane.

For example, the provided acoustic property values comprise values representative for acoustic impedance against said patient's tympanic membrane of said ear.

For example, the provided acoustic property values comprise values representative for acoustic admittance against said patient's tympanic membrane of said ear.

For example, the provided acoustic property values comprise values representative for absorbance.

Then, the acoustic measurement device may act as a tympanometer and a tympanogram can be obtained.

For example, the provided acoustic property values comprise values representative for otoacoustic emission.

The acoustic measurement device according to the application is especially suitable for providing acoustic property values for objective ear-condition evaluation for human's ears, but the application is not limited thereto. The concept of the device and the instrument according to the application could be applied for objective ear-condition evaluation of animals as well.

Basically, the membrane of each of the pumps of the pump arrangement can be formed in any suitable way. Very beneficial configurations can be achieved in terms of compactness and size-reduction of the pump arrangement if the at least two pumps are configured to act as membrane pumps for applying the air-pressure control procedure and particularly if they are formed as membrane pumps. Their miniature size allows an easier handling of the device and consequently an easier handling of the entire instrument according to the application.

In preferred variants of the application, the acoustic measurement device further comprises an acoustic input unit that is configured to capture acoustic signals representative for the air-pressure levels within the ear canal. The acoustic measurement device may comprise a control device that is configured to control the air pump arrangement. For example, the control device may comprise any form of regulation algorithm/controller to control the air-pump arrangement. For example, the control device may comprise a proportional—integral—derivative (PID) controller to control the air-pump arrangement, in particular using a regulation algorithm to perform for example constant pressure-sweep rates. This is particularly beneficial when the acoustic measurement device is used in tympanometry. The regulation algorithm may be based on an air pressure measured by a pressure sensor close to the acoustic input unit. The acoustic measurement device may further comprise a processing device that is configured to further process the captured acoustic signals.

In further preferred variants of the applications, the at least two pumps are formed as piezo-electric membrane pumps. The piezo-electric membrane pumps may then each be arranged fluidically in series with at least one flow-regulating component, wherein they are acting fluidically in parallel. Therein, each of the flow regulating components may be configured and arranged within the air pump arrangement such that at least one piezo-electric membrane pump is capable of working bidirectional when applying the air-pressure control procedure.

Therein, in very beneficial variants of the application, it is provided that the at least two pumps comprise a first pump and a second pump, where the first pump and the second pump being poled in opposing directions to each other.

So, in other words, the air pump arrangement may be configured such that the at least two pumps, preferably being (miniature) piezo-electric membrane pumps, are capable of working simultaneously to control the air pressure level within the air pressure control procedure in the ear canal.

The flow regulating components in the above-described configurations may be formed as flow resistors.

In some preferred variants of the application, an air pump arrangement provides a first piezo-electric membrane pump fluidically in series with a first flow resistor and a second piezo-electric membrane pump fluidically in series with a second flow resistor. The air pump arrangement may be configured and arranged such that pressure between the first flow resistor and said second flow resistor can be controlled in the ear-canal of the respective ear. Thereby, the air pump arrangement may essentially act in the manner analogous to a voltage divider, by maintaining and adjusting an inlet pressure and an outlet pressure at the first and the second piezo-electric membrane pump.

Further preferred variants of the application comprise an acoustic muffler that is provided and arranged at the ear probe. For example, the acoustic muffler may attenuate acoustic noise generated by the air-pump arrangement from entering the ear canal and interfering with ongoing acoustic measurement. The acoustic muffler may be configured to constitute the flow regulating components described above, preferably in the form of a flow resistor. For example, the acoustic muffler may consist of a network of narrow tubes and cavities, configured to attenuate acoustic noise and acting in a manner of a flow resistor.

In certain preferred variants of the application, (for example, when the acoustic measurement device is used for tympanometry, and hence acts in the form of a tympanometer), its air pump arrangement, in the resting position within the patient's ear, is configured to apply the air pressure control procedure in the form of maintaining essentially a single air pressure level during the procedure. Conventionally, the air pressure level lies in the range of −600 to +400 daPa.

In addition, or as an alternative, the air pump arrangement, in the resting position, may be configured to apply the air pressure control procedure in the form of performing varying air pressure levels during the respective procedure with varying air pressure levels during the procedure ranging between around −600 daPa to +400 daPa. In such a case, preferably, the respective procedure follows the standardized procedure of varying air pressure for different instrumental types according to IEC 60645-5 (2005). For example, the air pump arrangement, in the resting position, may be configured to perform these varying air-pressure levels with an adjustable air-pressure sweep rate. Thereby, a tympanogram can be obtained in a reliable manner but with a more handy and compact acoustic measurement device thanks to the use of membrane pumps, in particular in the form of miniature piezo-electric membrane pumps.

The acoustic measurement device may be configured to provide acoustic property values representative for the patient's middle-ear in reaction to a first pressure control procedure of the air pressure control procedure, applied by the at least two pumps of said air pump arrangement across the patient's tympanic membrane of the ear.

The first pressure control procedure may contain performing varying air pressure levels during the procedure ranging between around −600 daPa to +400 daPa. Therein, the provided acoustic property values may be values representative for acoustic impedance against the patient's tympanic membrane of the respective ear to be diagnosed. In such a configuration for tympanometry, the air pump arrangement, in the resting position, may be configured to perform the varying air-pressure levels with an adjustable air pressure sweep rate. Preferably, also here, the air pump arrangement is capable of performing the air pressure sweep rates following the standardized procedure according to IEC 60645-5 (2005).

In addition, or as an alternative, the acoustic measurement device may be configured to provide acoustic property values representative for the patient's inner ear in reaction to a second pressure-control procedure of the air-pressure control procedure, applied by the at least two pumps of the pump arrangement across the patient's tympanic membrane of the ear.

The second pressure control procedure may contain performing and maintaining essentially a single air-pressure level during the procedure. The essentially single air pressure level performed may lie in the range of −600 to +400 daPa. The acoustic measurement device may be configured to act as a hearing diagnostic instrument for pressurized acoustic-reflex measurement.

In addition, or as an alternative, the acoustic measurement device may be configured to provide acoustic property values representative for the patient's inner-ear in reaction to a third pressure control procedure of the air-pressure control procedure, applied by the at least two pumps of the pump arrangement across the patient's tympanic membrane of the ear.

The third pressure control procedure may contain performing and maintaining essentially a single air pressure level during the procedure. The essentially single air pressure level performed may lie in the range of −600 to +400 daPa. The acoustic measurement device may be configured to act as hearing diagnostic instrument for otoacoustic-emission measurement.

According to a further aspect, the present application relates to a diagnostic instrumental arrangement that is configured to provide at least one objective ear-condition parameter of a patient's ear, in particular of a human's ear. The diagnostic instrumental arrangement comprises an acoustic measurement device according to any of the configurations or variants according to the application as described above. Furthermore, an acoustic input unit is provided and configured to capture acoustic signals representative for the air-pressure levels within the ear canal. Further, a control device is provided that is configured to control the pump arrangement according to any of the configurations or variants according to the application as described above. Finally, the diagnostic instrumental arrangement comprises a processing device configured to further process the captured acoustic signals to an evaluation device, the evaluation device being configured to execute an evaluation process to the processed acoustic signals associated to the air-pressure control procedure to obtain the at least one objective ear-condition parameter the said patient's ear.

The diagnostic instrumental arrangement may be is mechanically connectable to a stand-alone device and/or may be operated via a mobile end device, in particular a tablet or a smartphone.

According to a further aspect, the present application relates to an objective ear-condition evaluation method which uses a diagnostic instrumental arrangement as described above with an acoustic measurement device according to any one of the configurations or variants of the application as described above.

It is contemplated that the acoustic measurement device may comprise said air-pump arrangement, which comprises at least one pump (such as only one pump), wherein said at least one pump comprising a movable element in the form of a membrane. Further, said air-pump arrangement may comprise at least one flow regulating component, such as one or two flow regulating components.

Further preferred variants of the present application will become apparent from the dependent claims and the following description of a preferred embodiment of the acoustic measurement device and instrument arrangement which refers to the appended figures.

DETAILED DESCRIPTION OF THE APPLICATION

In the following, an example of an acoustic measurement device 1 is shown and described, which comprises an exemplary air pump arrangement 2 according to the application. The air pump arrangement 2 may comprise a first and a second pump. The first and/or the second pump may be a membrane pump. For example, the first and/or the second pump may be a piezo-electric membrane pump. For example, the first and/or the second pump may be a miniature piezo-electric membrane pump. The acoustic measurement device 1 may be used in a diagnostic instrumental arrangement (not further shown here).

Figure 1:
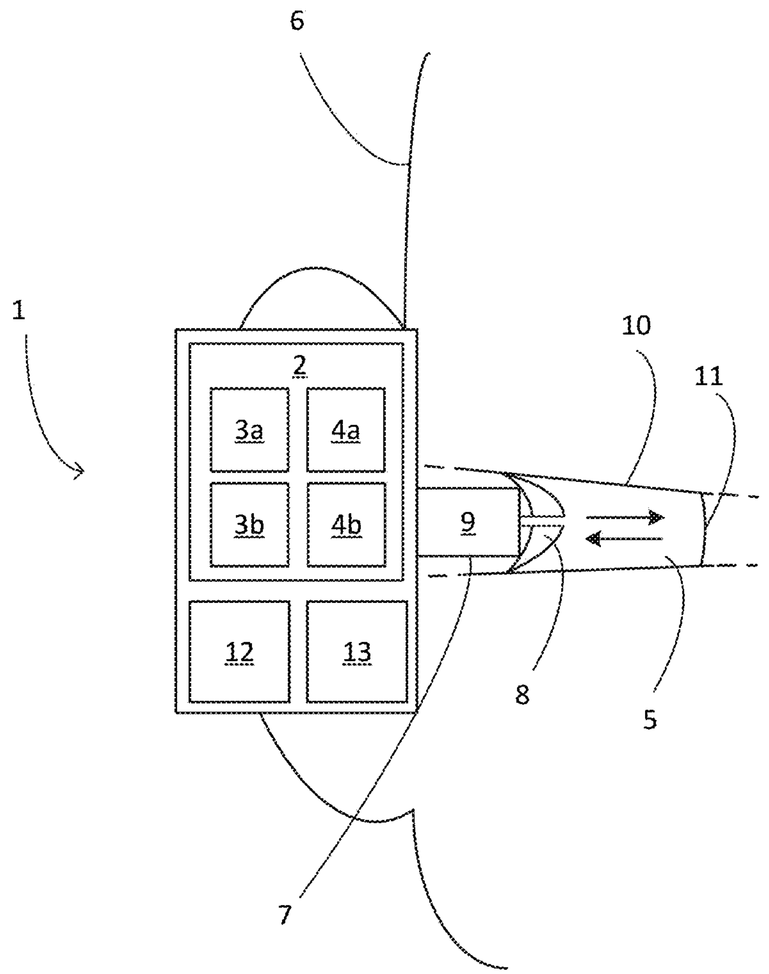
FIG. 1 shows an exemplary acoustic measurement device according to the application.

In FIG. 1, it is shown that the air-pump arrangement 2 of the acoustic measurement device 1 provides a first pump 3*a* (e.g. a miniature piezo-electric membrane pump) fluidically in series with a first flow resistor 4*a* and a second pump 3*b* (e.g. a miniature piezo-electric membrane pump) fluidically in series with a second flow resistor 4*b*. The air-pump arrangement 2 is configured and arranged such that pressure between the first flow resistor 4*a* and said second flow resistor 4*b* can be controlled in the ear-canal of the respective ear. Thereby, the air pump arrangement 2 essentially acts in the manner analogous to a voltage divider, by maintaining and adjusting an inlet pressure and an outlet pressure at the first and the second pump 3*a*, 3*b*.

Further, in FIG. 1, it is shown that at least part of said acoustic measurement device 1 may be positioned within an ear canal 5 of a patient 6 and be configured to take a resting position within said ear canal 5. The acoustic measurement device 1 may comprise an ear probe 7 positioned at least partly within said ear canal 5.

The ear probe 7 may comprise an ear tip 8, which may be releasably attached to an ear-probe body 9. When the ear probe 7 has been inserted into the ear canal 5 (and take a resting position), the ear tip 8 may provide a barometric seal toward the ear-canal walls 10 of the ear canal 5. The ear probe 7 may provide a stimulus into the ear of the patient 6 in a direction towards the eardrum 11 and receive a reflected part of said stimulus (i.e. capture acoustic signals), as indicated by the two arrows located in the ear canal 5.

The acoustic measurement device 1 may further comprise a control device 12 configured to control said pump arrangement 2.

The acoustic measurement device 1 may further comprise a processing device 13 configured to process said captured acoustic signals. An evaluation device of said processing device 13 may be configured to execute an evaluation process to said processed acoustic signals associated to an air-pressure control procedure to obtain at least one objective ear-condition parameter for said patient's 6 ear.

Preferably, the acoustic measurement device 1 is used for tympanometry, hence acts in the form of a tympanometer. However, in addition, the acoustic measurement device 1 may also be configured to perform diagnostic methods for pressurized acoustic-reflex measurement or diagnostic methods for otoacoustic-emission measurement.

The air pump arrangement 2 may be configured to apply an air pressure control procedure in the form of maintaining essentially a single air pressure level during the procedure. For example, the air pressure level then lies in the range of −600 to +400 daPa.

In addition, the air pump arrangement 2 may be configured to apply the air pressure control procedure in the form of performing varying air pressure levels during the respective procedure with varying air pressure levels during the procedure in the range of around −600 daPa to +400 daPa. The air pump arrangement 2 may be capable of performing the standardized procedures of varying air pressure for different instrumental types according to IEC 60645-5 (2005), which will be described by way of an example in the context with FIGS. 2 to 4 below.

Figure 2:
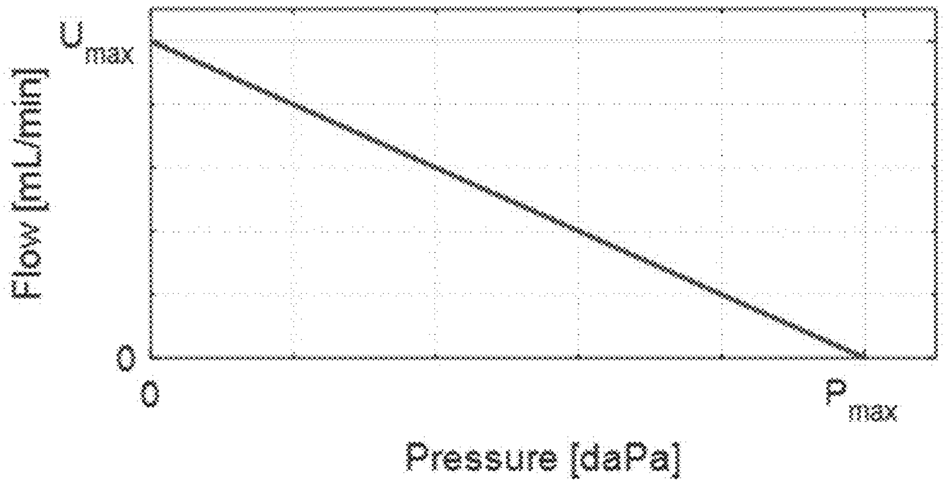
FIG. 2 shows a typical pressure-flow relationship of a typical membrane pump operated at its maximum power.

In FIG. 2, a typical relationship between maximum pressure $P_{(max)}$ and maximum flow $U_{max}$ of a single membrane pump (herein 3*a* or 3*b*), as known in the art operated at maximum power is illustrated. Decreasing the power delivered to the pump results in an offset parallel to this linear relationship.

Figure 3:
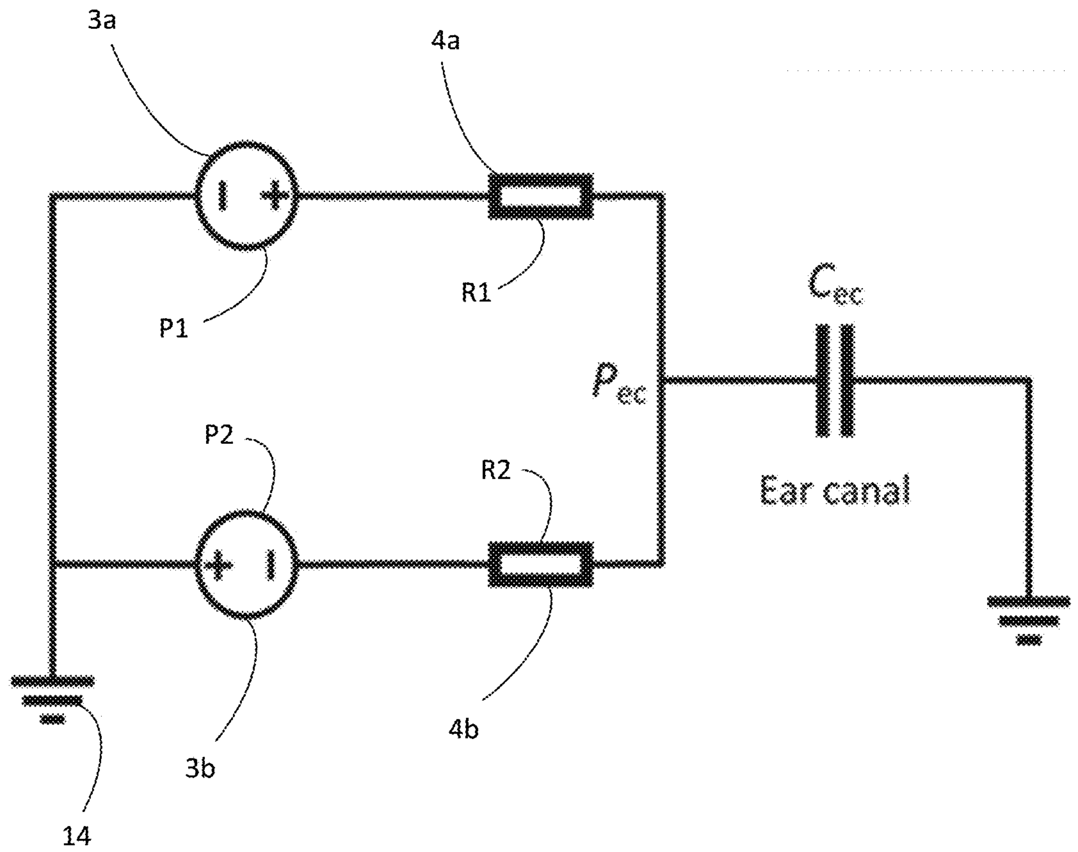
FIG. 3 shows a schematic illustration of an example according to the application of an electrical-analog circuit of two membrane pumps, represented by sources, connected to the volume of the ear-canal, represented by a capacitor, each in series with a flow resistor. Ground represents ambient pressure.

FIG. 3 illustrates the operating principle of the air pump arrangement 2 of the acoustic measurement device 1 by an electrical-analog circuit of the two membrane pumps 3*a*, 3*b*, represented by sources, connected to the volume of the ear-canal, represented by a capacitor $C_{ec}$, each in series with a flow regulating component in the form of the flow resistor 4*a*, 4*b*. The ground 14 represents ambient pressure.

Unlike a regular membrane-pump arrangement where two membrane pumps, each one being fluidically in series with one check valve, never operate simultaneously, the air pump arrangement 2, as given in FIG. 3, is based on simultaneous operation of the two membrane pumps formed as membrane pumps 3*a*, 3*b*.

While this configuration of air-pump arrangement 2 restricts the total flow through the system (compared to the case of no flow resistors), it allows accurately controlling the pressure between the two flow resistors 4*a*, 4*b*, i.e., in the ear canal, in a manner analogous to a voltage divider, by maintaining and adjusting the pressure at the outlet and inlet of the membrane pumps 3*a* and 3*b*, respectively and, thus, the flow through the resistors 4*a*, 4*b*. That is, maintaining a constant air pressure in the ear canal requires continuous operation of one membrane pump (3*a* or 3*b*).

This is opposed to the prior art pumps used in acoustic measurement devices, as piston pumps, peristaltic pumps, and gear pumps, where maintaining a constant ear-canal pressure simply requires stopping the pump.

In particular, the air pump arrangement 2 solves the issue associated with regular membrane pumps of not being able to control the flow through the membrane pump 3*a*, 3*b* due to a negative pressure drop in the flow direction because the pressure drops in the system occur across the two flow resistors 4*a*, 4*b*. That is, each membrane pump 3*a*, 3*b* can generate a change in pressure between the membrane pump 3*a*, 3*b* and flow resistor 4*a*, 4*b*, regardless of the pressure in the ear canal, and force a larger flow through the resistor than dictated by the ear-canal-to-ambient pressure difference.

Depending on the flow resistances $R_1$ (associated with flow resistor 4*a*) and $R_2$ (associated with flow resistor 4*b*), operating membrane pumps 3*a* and 3*b* at some constant power results in a given point of operation on the pressure-flow relationship in FIG. 2 and the pressures $P_1$ and $P_2$. Disregarding non-linear effects by assuming that the flow resistances $R_1$ and $R_2$ of each flow resistor 4*a* and 4*b* does not depend on the flow, the pressure in the ear canal $P_{ec}$ when the system is in a steady state can be calculated based on the voltage-divider equation, $$P_{ec} = \frac{(P_1 - P_2)R_2}{R_1 + R_2}.$$

Thus, manipulating $P_1$ and $P_2$ by controlling the drive power to each membrane pump 3*a*, 3*b* any pressure can be achieved in the ear canal $P_{ec}$ and this pressure can be altered in any direction.

Deriving the pump drive powers that yield a constant-rate ear-canal pressure $P_{ec}(t)$ is more complicated because the pressure-flow operational point of each pump changes temporarily in response to sudden changes in power until a steady state has been reattained. Assuming that the pressure-flow operational point remains constant and that a change in pump powers result in proportional changes in $P_1(t)$ or $P_2(t)$, the ear-canal pressure response $P_{ec}(t)$ resulting from step changes in pump drive powers takes the form of an exponential decay, $$P_{ec}(t)=ae^{-bt}+c.$$

The constants a, b, and c are mathematical expressions comprised by $R_1$, $R_2$, the compliance of the ear canal $C_{ec}$ (which is inversely proportional to its volume), and the initial and final values of the pressure step functions $P_1(t)$ and $P_2(t)$. Consequently, the pressures $P_1(t)$ or $P_2(t)$ required to produce linear changes to the ear-canal pressure $P_{ec}(t)$ when operating only one membrane pump 3*a* or 3*b* at a time can be immediately calculated.

While it is possible to predict how the membrane pumps 3*a*, 3*b* should be driven to achieve ear-canal pressure with constant pressure sweep rates with the given approximations and a given ear-canal volume, practical application in ear-canals of varying volumes require a regulation algorithm. In such a case, for example, a PID controller is used to achieve these constant pressure-sweep rates. For example, this regulation algorithm is based on the air pressure measured by a pressure sensor close to the ear probe.

Accordingly, the acoustic measurement device may comprise a pressure sensor.

A standard air-pressure procedure required to generate a tympanogram may usually consists of three principal steps.

First, the air pump arrangement is used to pump to a desired starting pressure. In terms of the pressure difference across the tympanic membrane, this starting pressure may be within at least the range of −600 to +200 daPa for type-1 instruments and −200 to +200 daPa for type-2 and type-3 instruments (IEC 60645-5 (2005)), although instruments often support wider pressure ranges, e.g., −600 to +400 daPa (see FIG. 4).

The second step involves a pressure sweep, specified by a constant pressure sweep rate in units of daPa/s (positive or negative depending on the direction of the sweep), from the starting pressure to the stopping pressure of opposite operational sign. Type-1 instruments must be capable of maintaining a constant sweep rate of 50 daPa/s with a tolerance of ±10 daPa/s for the duration of the sweep (IEC 60645-5 (2005)), passing the 0-daPa pressure-difference point. The acoustic measurements of the middle ear may be acquired during this pressure sweep of the second step.

Finally, as the third step, the ear-canal pressure is returned to ambient pressure in a controlled manner to minimize patient discomfort, concluding the pressurization procedure.

Other air-pressure procedures used in tympanometry may include a manual tympanogram, where the operator adjusts the pressure in the ear canal using, e.g., a slider, while observing the acoustic changes to the middle ear.

Figure 4:
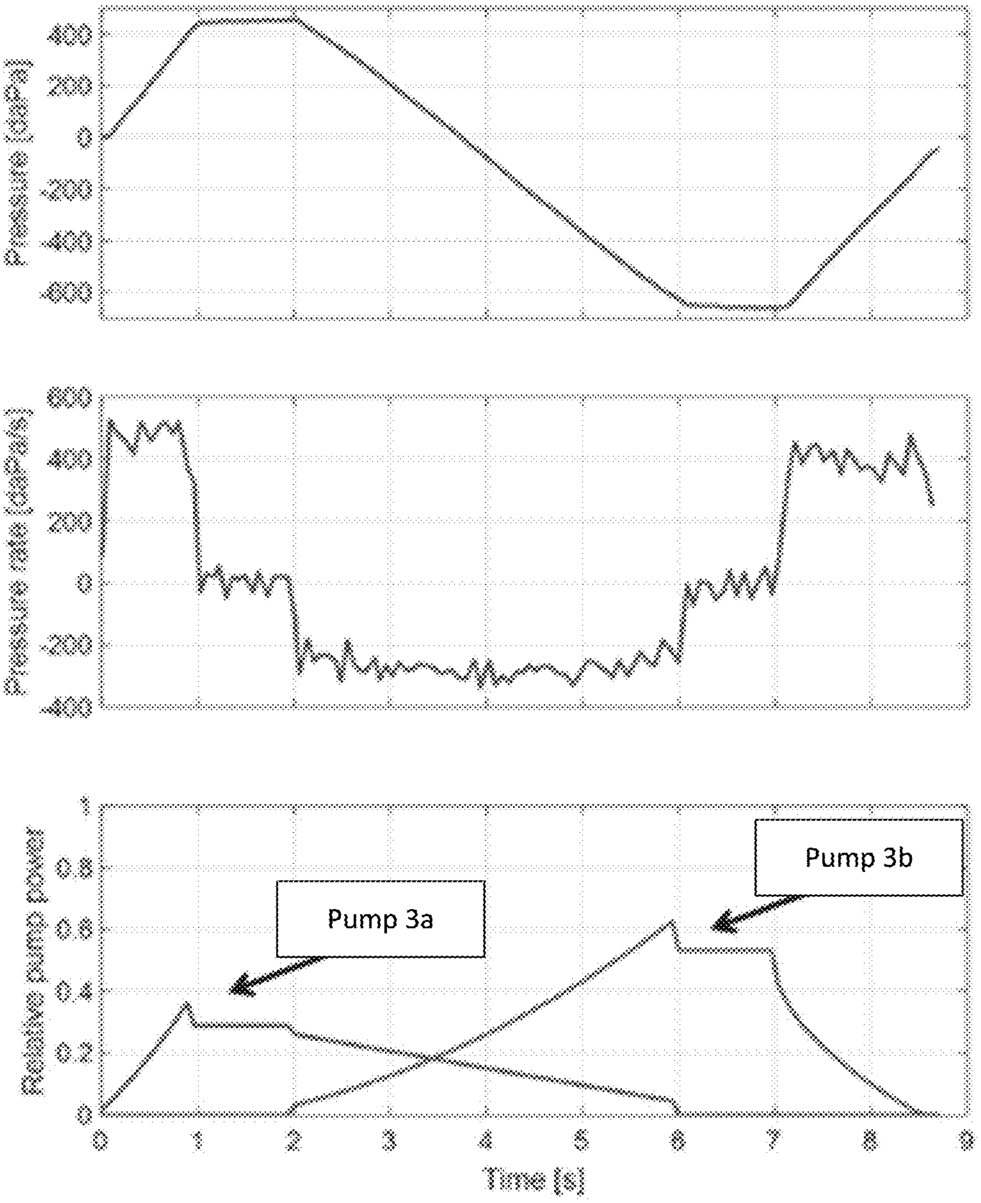
FIG. 4 shows a schematic illustration of an example according to the application of producing a tympanometric air-pressure procedure using two membrane pumps in terms of the ear-canal pressure (top), the pressure rate (middle), and the relative pump power of the two pumps (bottom).

FIG. 4 now exemplifies the application of the acoustic measurement device 1 with two membrane pumps 3*a*, 3*b* and the two (precision-orifice) flow resistors 4*a*, 4*b* to produce the above described standardized 3 step sequence of air pressure procedure of a tympanogram in a small cavity in terms of the pressure measured by the pressure sensor (top), the pressure rate (middle), and the relative pump drive power of the two membrane pumps 3*a*, 3*b* (bottom).

The sequence shown in FIG. 4 is not based on a regulation algorithm; instead, pump drive-power curves were predefined with trial-and-error adjustments to produce approximately linear pressure changes in the given cavity volume. It is evident how only membrane pump 3*a* is required for the initial linear pressurization of the ear canal, and only membrane pump 3*b* is required for the concluding linear depressurization. Notice also the simultaneous operation of the two membrane pumps 3*a*, 3*b* during the pressure sweep, crossing the 0-daPa point. For the pressure sweep in this example, the power of pump 3*a* was set to linearly decrease over some specified time while the power of pump 3*b* was adjusted to create a linear pressure sweep.

It is intended that the structural features of the devices, arrangements and instruments described above, either in the detailed description and/or in the claims, may also account for the corresponding process as it is claimed by the objective ear-condition evaluation method using such devices, arrangements and instruments.

The particular features, structures or characteristics may be combined as suitable in one or more embodiments of the disclosure. The previous description is provided to enable any person skilled in the art to practice the various aspects described herein. Various modifications to these aspects, variants and configurations will be readily apparent to those skilled in the art, and the generic principles defined herein may be applied to other aspects.

Accordingly, the scope should be judged in terms of the claims that follow.

REFERENCES

IEC 60645-5, 2005 *"Instruments for the measurement of aural acoustic impedance/admittance*. (International Electrotechnical Commission, Geneva, Switzerland)"

The invention claimed is:

1. An acoustic measurement device configured to provide acoustic property values for objective ear-condition evaluation of a patient's ear, wherein:

at least part of said acoustic measurement device is configured to be positioned within an ear canal of said patient and configured to take a resting position within said ear canal, said acoustic measurement device comprises an ear probe, said acoustic measurement device further comprises an air-pump arrangement, said air-pump arrangement, at least in said resting position, being in fluid connection with said ear canal through at least one tube running via said ear probe, said air-pump arrangement, in said resting position, is configured to perform an air-pressure control procedure, consisting of applying at least one air-pressure level across said patient's tympanic membrane of said ear, said acoustic measurement device, in said resting position, is configured to provide acoustic property values in reaction to said air-pressure control procedure applied by said air-pump arrangement across said patient's tympanic membrane of said ear, said air-pump arrangement comprises at least two pumps, including a first pump and a second pump, wherein each of said at least two pumps comprises a movable element in the form of a membrane, and the first pump and the second pump are poled in opposing directions to each other, and said air-pump arrangement is configured such that said at least two pumps are configured to work simultaneously to control said air pressure level within said air-pressure control procedure in said ear canal.

2. Acoustic measurement device according to claim 1, further comprising:

an acoustic input unit configured to capture acoustic signals representative for said air-pressure levels within said ear canal, a control device configured to control said air-pump arrangement, and a processing device configured to further process said captured acoustic signals.

3. Acoustic measurement device according to claim 1, wherein:

said at least two pumps are formed as piezo-electric membrane pumps and are each arranged fluidically in series with at least one flow regulating component, wherein the two piezo-electric membrane pumps are arranged parallel to each other, and wherein:

each said at least one flow regulating component is configured and arranged within said air-pump arrangement to allow said two piezo-electric membrane pumps to work bidirectionally when performing said air-pressure control procedure.

4. Acoustic measurement device according to claim 3, wherein:

said flow regulating components consist of a network of narrow tubes and cavities configured to attenuate acoustic noise and act in a manner of a flow resistor.

5. Acoustic measurement device according to claim 1, wherein:

said at least two pumps are formed as piezo-electric membrane pumps, and a first piezo-electric membrane pump of the at least two pumps is fluidically in series with a first flow resistor and a second piezo-electric membrane pump of the at least two pumps is fluidically in series with a second flow resistor, wherein said first piezo-electric membrane pump and said second piezo-electric membrane pump are arranged parallel to each other, wherein:

said air-pump arrangement is configured and arranged such that pressure between said first flow resistor and said second flow resistor is controlled in said ear-canal of said ear, and said air-pump arrangement thereby acting in a manner analogous to a voltage divider by maintaining and adjusting an inlet pressure and an outlet pressure at each of said first and said second piezo-electric membrane pumps.

6. Acoustic measurement device according to claim 1, wherein:

said air-pump arrangement, in said resting position, is configured to perform said air-pressure control procedure in the form of maintaining essentially a single air pressure level during said procedure, wherein said air pressure level lies in the range of −600 to +400 daPa, or said air-pump arrangement, in said resting position, is configured to perform said air-pressure control procedure in the form of producing varying air pressure levels during said procedure, wherein said varying air pressure levels during said procedure range between around −600 daPa to +400 daPa, wherein said air-pump arrangement, in said resting position, is configured to produce said varying air-pressure levels with an adjustable air-pressure sweep rate.

7. Acoustic measurement device according to claim 1, wherein:

said acoustic measurement device is configured to provide acoustic property values representative for said patient's middle-ear in reaction to said air-pressure control procedure, performed by said at least two pumps of said air-pump arrangement across said patient's tympanic membrane of said ear, wherein:

said air-pressure control procedure comprises producing varying air pressure levels during said procedure, wherein said varying air pressure levels during said first pressure air-pressure control procedure range between around −600 daPa to +400 daPa, wherein:

said air-pump arrangement, in said resting position, is configured to produce said varying air-pressure levels with an adjustable air pressure sweep rate, and said acoustic measurement device is configured to act as a tympanometer.

8. Acoustic measurement device according to claim 1, wherein:

said acoustic measurement device is configured to provide acoustic property values representative for said patient's inner ear in reaction to said air-pressure control procedure, performed by said at least two pumps of said air-pump arrangement across said patient's tympanic membrane of said ear, wherein:

said air-pressure control procedure comprises performing and maintaining a single air pressure level during said procedure, said single air pressure level lying in the range of −600 to +400 daPa, and said acoustic measurement device is configured to act as a hearing diagnostic instrument for pressurized acoustic-reflex measurement.

9. Acoustic measurement device according to claim 1, wherein:

said acoustic measurement device is configured to provide acoustic property values representative for said patient's inner-ear in reaction to said air-pressure control procedure, performed by said at least two pumps of said air-pump arrangement across said patient's tympanic membrane of said ear, wherein:

said air-pressure control procedure contains producing and maintaining a single air pressure level during said procedure, said single air pressure level lying in the range of −600 to +400 daPa, and said acoustic measurement device is configured to act as a hearing diagnostic instrument for otoacoustic-emission measurement.

10. Acoustic measurement device according to claim 1, wherein the acoustic measurement device further comprises a control device configured to control said air-pump arrangement.

11. A diagnostic instrumental arrangement configured to provide at least one objective ear-condition parameter of a patient's ear, comprising:

an acoustic measurement device according to claim 1, and a processing device configured to further process said captured acoustic signals and transmit said processed signals to an evaluation device, wherein said evaluation device is configured to execute an evaluation process using said processed acoustic signals associated with said air-pressure control procedure to obtain said at least one objective ear-condition parameter for said patient's ear.

12. A diagnostic instrumental arrangement according to claim 11, wherein said diagnostic instrumental arrangement is mechanically connectable to a stand-alone device or is operated via a mobile end device.

* * * * *